United States Patent [19]

Tikkanen et al.

[11] Patent Number: 5,716,792
[45] Date of Patent: Feb. 10, 1998

[54] STREPTOCOCCUS SUIS ADHESIN PROTEIN AND METHOD FOR PRODUCING IT

[76] Inventors: Kaarina Tikkanen, Maaherränkatu 35 as 9, FIN-70100 Kuopio; Jukka Finne, Katajanokanranta 3 A 5, FIN-00160 Helsinki, both of Finland

[21] Appl. No.: 500,895

[22] PCT Filed: Jan. 28, 1994

[86] PCT No.: PCT/FI94/00039

§ 371 Date: Aug. 29, 1995

§ 102(e) Date: Aug. 29, 1995

[87] PCT Pub. No.: WO94/17103

PCT Pub. Date: Aug. 4, 1994

[30] Foreign Application Priority Data

Jan. 29, 1993 [FI] Finland ................... 930413

[51] Int. Cl.$^6$ ............................ G01N 33/569
[52] U.S. Cl. .................. 435/7.34; 424/54; 424/165.1
[58] Field of Search ............. 435/7.34; 424/165.1, 424/54

[56] References Cited

U.S. PATENT DOCUMENTS 5,202,113  4/1993  London ........................ 424/54

OTHER PUBLICATIONS

Dialog Information Services, file 155, Medling, Dialog accession No. 08306030, Medline accession No. 93016030, Liukkonen J. et al: "Identification of N–acetylneuraminyl alpha 2–3 et al"Oct. 15, 1992.

"Hemagglutination Activities of Gropu B, C, D, and G Streptococci: Demonstration of Novel Sugar–Specific et al" Kural et al, pp. 384–389 Infection and Immunity, Feb. 1989, American Society for Microbiology.

"Identification of N–Acetylneuraminyl a2–3 Poly–N–Acetyllactosamine Glycans as the Receptors et al" Liukkonen et al, The Journal of Biological Chemistry, vol. 267, No. 29, Oct. 15, 1992, pp. 21105–21111.

Mayra–Makinen et al, Journal of Applied Bacteriology, 1983, pp. 241–245, vol. 55.

Alpert et al, Biochemistry, 1985, pp. 959–964, vol. 24.

Haataja et al, The Journal of Biological Chemistry, vol. 268, #6, Feb. 1993, pp. 4311–4317.

Elliott et al, The Journal of Experimental medicine, vol. 145, 1977, pp. 490–499.

Kehoe, Michael A., Vaccine, vol. 9, Nov. 1991, pp. 797–806.

Gottschalk et al, Canadian Journal of Vet. Res., Jul. 1991, vol. 55(3), pp. 302–304.

Catty et al, In Antibodies, vol. II, 1990, Chapter 4, pp. 97–123.

Primary Examiner—James C. Housel
Assistant Examiner—Ginny Allen Portner
Attorney, Agent, or Firm—Nixon & Vanderhye

[57] ABSTRACT

Disclosed is *streptococcus suis* adhesin protein, a method for producing it, and antibodies against the adhesin protein. Pigeon ovomucoid or a synthetic derivative is used in the identification of the adhesin protein. The adhesin protein and the antibodies may be used both diagnostically and therapeutically. The adhesin protein and its derivatives and fragments and the corresponding polynucleotides can also be used as a vaccine.

11 Claims, No Drawings

1

STREPTOCOCCUS SUIS ADHESIN PROTEIN AND METHOD FOR PRODUCING IT

BACKGROUND

1. Field of the Invention

The invention relates to a *Streptococcus suis* adhesin protein, biologically or immunologically active derivatives and fragments thereof, a method for producing the adhesin protein, and an antibody raised against the adhesin protein, or the derivative or fragment thereof. The invention also relates to the use of pigeon ovomucoid or a synthetic derivative in the identification of the adhesin protein. The adhesin protein according to the invention, the derivatives and fragments thereof and their antibodies can be used diagnostically, therapeutically, and prophylactically.

*S. suis* bacteria (the Lancefield group D) are known to cause meningitis, pneumonia, arthritis and sepsis in pigs. *S. suis* type 1 causes mainly septicemia and meningitis in newborn pigs, while type 2 causes meningitis in pigs about 3 to 10 weeks in age, and may also be infectious to humans. There are at least 29 capsular types identified, many of which cause disease in pigs. Concentration of pig breeding and increasing animal densities facilitate the spreading of infections, and infectious diseases caused by *S. suis* become more common. For this reason, the development of a diagnostic technique and a vaccine is of vital importance in the identification and prevention of meningitis and other serious infections. Selective preventive measures directed to pig breeders may also be possible.

2. Prior art

The first event in the establishment of an infectious disease is the adhesion of bacteria to the surface of host cells (Beachey, E. H. (1981) *J. Infect. Dis.* 143, 325–345). The adhesion of bacteria is often mediated by an adhesin protein which occurs on the bacterial surface and adheres specifically to cell surface receptor structures. As a consequence, adhesin is well-suited for the development of a vaccine as the antibodies are directed specifically against a factor necessary for the bacterium; in addition, the specificity allows detrimental side effects to be avoided.

A wide variety of adhesins are known, but in many cases their exact structure and mechanism still remain unknown. They are proteins that recognize the receptors of the host cell specifically, the receptors being usually carbohydrate structures. Various bacterial adhesins and carbohydrate structures recognized by them are described e.g. in Sharon, N., (1987) *FEBS Letters*, 217, 145–157.

*E. coli* and many other gram negative bacteria adhere to specific molecules on the surface of the host cell by lectin-like bacterial adhesins. Usual adhesin receptors include the sugar components of glycolipids and glycoproteins. Adhesins are often attached to hair-like structures called fimbriae (pili) on the surface of the bacterial cell. There are many different types of fimbriae; they vary with respect to both structure and sugar specificity.

As there are often bacterial receptor structures on erythrocytes, bacteria adhere to these structures and agglutinate erythrocytes in vitro. Bacterial cultures may express three or four hemagglutinins (adhesins), each having a different binding specificity. Accordingly, the bacterium is capable of adhering to various cell types.

In enterobacteria studies, adhesion reactions are divided into two main classes: mannose sensitive (MS) reactions in which the hemagglutination reaction is inhibited by α-mannosides, and mannose resistant (MR) reactions in which the hemagglutination cannot be inhibited by α-mannosides. *E. coli* type 1 fimbriae (MS structure) consists almost solely of identical 17 kDa subunits. Several MR adhesins recognize an α-Gal(1-4)-β-Gal structure (P-specific adhesin) or an α-NeuNAc-(2-3)-β-Gal structure (S-specific adhesin). In general, purified fimbriae consist of subunits having a molecular weight varying between 15 and 22 kDa.

Adhesin protein is usually a distinct protein attached to the tips or sides of the fimbriae; it may also be attached directly to the outer membrane of the bacterium. In certain bacterial strains the surface of the bacterial cell contains adhesin protein even in the absence of fimbriae. In such cases, adhesins may form an adhesin capsule around the bacterium. The size of the non-fimbrial adhesins of *E. coli* varies between 13 and 28 kDa (Jann, K. and Hoschutzky. H. (1990), *Current Topics in Microbiology and Immunology* 151, 55–70).

It is known that streptococci bind to various soluble proteins and glycoproteins, whereas their oligosaccharide specificity is mostly unknown. Their specific binding to epithelial cells is also nearly unknown. Certain *Streptococcus sanguis* strains recognize galactose and sialic acid containing structures (Murray, P. A., Levine, M. J., Tabak, L. A., and Reddy, M. S. (1982) *Biochem. Biophys. Res. Commun.* 106, 390–396). The binding of *Streptococcus pneumoniae* to epithelial cells is inhibited by GlcNAcβ1-3Gal (Andersson, B., Porras, O., Hanson, L. A., Lagergard, T., and Svanborg-Eden, C. (1986) *J. Infect. Dis.* 153, 232–237), and this bacterium has been reported to bind to GalNAcβ1-4Gal-containing glycolipids in the lung (Krivan, H. C., Roberts, D. D. and Ginsburg, V. (1988) *Proc. Natl. Acad. Sci., USA.* 85, 6157–6161).

*S. mitis* adheres to the surface of a tooth and contributes to the formation of dental plaque. A sialic-acid-binding adhesin has been successfully isolated from this bacterial strain. The sialic-acid-binding protein had at least two disulphide-bound subunits of 96 kDa and 70 kDa. Both subunits bound N-acetylneuraminic acid-β2-3-galactose-β1-3-N-acetylgalactosamine (Murray, P. A., Levine, M. J., Reddy, M. S., Tabak, L. A., Bergey, E. J. (1986) *Infect. Immun.* 53, 359–365). The galactose-binding adhesin of *S. sanguis* was determined to have a molecular weight of about 20 kDa, and its isoelectric point was in the range 8.5–9 (Nagata, K., Nakao, M., Shibata S., Shizukuishi, S., Nakamura R. and Tsunemitsu, A. (1983) *J. Periodontol.* 54, 163–172). In addition to this, a 36-kDa adhesin protein has been cloned from *S. sanguis* bacteria. The carbohydratic specificity of the cloned adhesin remains unknown, whereas it is known that adhesin adheres to saliva-coated hydroxyapatite through the mediation of a pH sensitive receptor (Ganeskumar, N., Song, M. and McBride, B. C. (1988) *Infect. Immun.* 56, 1150–1157).

*S. suis* is an important pathogen in pigs. It colonizes the tonsils or nostrils of piglets and causes serious infections. There are several capsular serotypes, for which reason no vaccine effective against all *S. suis* types is available. The capsular polysaccharides and surface proteins of *S. suis* have been reported to play a role in the pathogenesis, but the molecular mechanism of the infection has remained unknown. Two strains of *S. suis* bacteria have been shown to bind to sialylated poly-N-acetyllactosamine glycans (Liukkonen J., Haataja, S., Tikkanen, K., Kelm, S., and Finne, J. (1992) *J. Biol. Chem.* 267, 21105–21111). However, the hemagglutination caused by most *S. suis* bacteria is inhibited by galactose, so that the galactose-recognizing adhesin is probably more common in *S. suis* bacteria than that mentioned above (Kurl, D., Haataja, S. and Finne, J. (1989) *Infect. Immun.* 57, 384-389).

Several attempts have been made to detach and isolate adhesins by heat treatment and/or extraction. The adhesin of *Proteus mirabilis* was isolated by heat treatment (65° C., 20 min, 50 mM sodium phosphate (pH 7.2) with 2M urea), and purified by gel filtration (Sepharose CL-4B) (Wray, S. K., Hull, S. I., Cook, R. G., Barrish, J. and Hull, R. A. (1986) *Infect Immun.* 54, 43-49). The lectin of *S. mitis* was separated by extracting the bacteria with lithium-3,5-diiodosalicylate, and a sialic-acid-binding protein was purified from the extract by gel filtration and affinity chromatography (Murray, P. A., Levine, M. J., Reddy, M. S., Tabak, L. A. and Bergey, E. J. (1986) *Infect. Immun.* 53, 359-365). A protein of *Streptococcus pyogenes* (the Lancefield group A) capable of adhering to the cardiac tissue and the basement membrane of kidney cells was successfully separated by treating the bacteria with alkali for 18 h (Stinson, M. W. and Bergey E. J. (1982) *Infect. Immun.* 35, 335-342). A non-fimbrial adhesin of *E. coli* was extracted by heating the bacterial suspension at 65° C. for 30 min (Goldhar, J., Perry, R., Golecki, J. R., Hoschutzky, H., Jann B., and Jann K. (1987) *Infect. Immun.*, 55, 1837-1842). Fimbriae were separated from the fimbrial *E. coli* by mechanical homogenization, and the adhesin protein was separated from the fimbrial homogenate by heat treatment (70° C., 1 h, PBS/5 mM EDTA) (Moch, T., Hoschutzky, H., Hacker, J., Kröncke, K. -D. and Jann, K. (1987) *Proc. Natl. Acad. Sci. USA* 84, 3462-3466). After detachment the adhesin protein has often been precipitated by ammonium sulphate precipitation, whereafter the adhesins have been purified further by various methods. Conventional methods used for the separation of adhesins, however, have not been suitable for the isolation of *S. suis* adhesins.

SUMMARY OF THE INVENTION

The isolation and characterization of the adhesin protein of *Streptococcus suis* have now been performed successfully. The invention thus relates to the adhesin protein or a biologically or immunologically active derivative or fragment thereof, which is characterized in that the adhesin protein binds to the Galβ1-4Gal disaccharide structure and comprises the amino acid sequence Ala-Ser-Pro-Ala-Glu-Ile-Ala-Ser-Phe-Ser-Pro-Ala-Pro-Leu-Ala (SEQ ID NO: 1). The adhesin protein according to the invention can be produced by a method wherein the *S. suis* strain is sonicated and the detached adhesin protein is pre-purified by a conventional protein purification technique, and then purified electrophoretically or chromatographically. Pigeon ovomucoid is preferably used in monitoring the purification of the adhesin protein. The invention also relates to antibodies raised against the adhesin protein, or a derivative or fragment thereof, and to a diagnostic method where the antibodies or adhesin protein, or a derivative or fragment thereof are used in an immunoassay method for detecting *S. suis* bacteria or for detecting antibodies directed to *S. suis* bacteria. The invention further relates to the use of the adhesin protein according to the invention or a derivative or fragment thereof as a vaccine, and to the use of the antibodies for passive immunization.

DETAILED DESCRIPTION OF THE INVENTION

The adhesin protein according to the invention can be detached from the surface of *S. suis* bacteria by sonication. After sonication it is advisable to add a protease-inhibitor to prevent proteolysis. The sonicate is then centrifuged, and the supernatant is recovered. The supernatant containing adhesin protein is preferably pre-purified by a conventional protein purification technique, such as ultrafiltration, dialysis, gel filtration, or precipitation by salt. It is preferable to use ammonium sulphate precipitation, and other proteins can be removed most preferably by an ammonium sulphate solution having a saturation degree of about 60%, whereafter the adhesin protein can be precipitated by an ammonium sulphate solution having a saturation degree of about 70%.

The actual purification may be carried out electrophoretically, e.g. by gel electrophoresis, or chromatographically, e.g. by affinity chromatography or immunoaffinity chromatography. Preferably a preparative native gel electrophoresis is applied. The native electrophoresis means an electrophoresis without sodium dodecylsulphate (SDS). It is particularly advantageous to use a continuous elution electrophoresis apparatus preferably cylindrical in shape. Fractions are collected from the apparatus and protein fractions having adhesin activity are recovered.

The biological activity of the adhesin protein of *S. suis* can be utilized in monitoring the purification of the adhesin protein. The adhesin protein is associated with the hemagglutination ability of *S. suis* bacteria, which can be inhibited by certain sugar compounds, such as by galactose and N-acetylgalactosamine or by galactose only, at millimolar concentrations. In the study of galactose-specific adhesin proteins, it is preferable to use sialidase-treated human erythrocytes. Hemagglutination tests and hemagglutination inhibition tests are described in Kurl, D. N., Haataja, S. and Finne J. (1989) *Infect. Immun.* 57, 384-389; and Haataja, S., Tikkanen, K., Liukkonen, J., Francois-Gerard, C. and Finne, J., (1993) Characterization of a Novel Bacterial Adhesion Specificity of *Streptococcus suis* Recognizing Blood-Group P Receptor Oligosaccharides, *J. Biol. Chem.* 268, No 6, p. 4311-4317 (1993).

Inhibition studies with mono- and oligo-saccharides show that the receptor structure of *S. suis* is Galα1-4Galβ1-4Glc. This forms the oligosaccharide part in the $p^k$ antigen of the blood group P glycolipids. On the other hand, hemagglutination inhibition tests and direct binding of glycoproteins and neoglycoproteins indicate that the $P_1$ antigen structure Galα1-4Galβ1-4GlcNAc is also recognized by the adhesin. Consistent with this, the adhesin binds strongly to the Galα1-4Gal disaccharide structure as compared with the α1-3, α1-6, α-galactose disaccharide derivatives. Inhibition studies with oligosaccharides show that the terminal α-galactose plays an important role in the binding of adhesin.

It has now been found that pigeon ovomucoid is an extremely effective inhibitor. 0.06 μg/ml of pigeon ovomucoid inhibits the hemagglutination induced by the *S. suis* strain 628 completely. Pigeon ovomucoid is a glycoprotein the terminal sequence of the glycan chains of which is Galα1-4Galβ1-4GlcNAc; it is described in Francois-Gerard, C., Gerday, C. and Beeley, J. G. (1979) *Biochem. J.*, 117, 679-685. This structure causes the *S. suis* adhesin protein to bind strongly to pigeon ovomucoid. Consequently, the pigeon ovomucoid also has the blood-group $P_1$ activity. Synthetic derivatives containing the Galα1-4Gal disaccharide structure can also be used in the identification of *S. suis* adhesin protein. E.g. Galα1-4Galβ1-4Glc-O-CETE-BSA has proved to be an extremely strong inhibitor in the hemagglutination inhibition.

The purification of the adhesin protein can be easily monitored by a simple pigeon ovomucoid binding test. The ovomucoid used in monitoring the purification may be labelled e.g. by a radioactive label. The test may be e.g. a spot test where a sample containing adhesin protein is pipetted onto a nitrocellulose paper, and the paper is then covered with the radio-actively labelled pigeon ovomucoid, incubated, and washed. The radioactivity bound to the paper is then determined. The intensity of the binding correlates with the hemagglutination activity of the strain.

Preferably the purification of the adhesin protein is monitored by the Western blot method, where the samples are subjected to a polyacrylamide gel electrophoresis, after which the proteins are transferred by an electric current onto a membrane which is then treated in a similar manner as the paper above. The S. suis sonicates from the different strains exhibit a single adhesin protein band moving at the same rate. The intensity of the band correlates with the hemagglutination activity. The band is also distinguishable when the hemagglutination-negative strains are used, though usually more weakly. A reason for this might be the phase variation associated with the adhesin protein, i.e. bacteria may express adhesin at a different level in different conditions. Another possible reason is the inhibitory effect of other surface structures, such as a capsule.

The above-described method allows the production of a S. suis adhesin protein which has a molecular weight of about 18,000, an isoelectric point of about 6.4, the N-terminal sequence of which is Ala-Ser-Pro-Ala-Glu-Ile-Ala-Ser-Phe-Ser-Pro-Ala-Pro-Leu-Ala (SEQ ID NO: 1), and the amino acid composition of which is:

| Amino acid | mol amino acid/mol protein |
| --- | --- |
| Asx = asparagine and/or asparaginic acid | 13 |
| Thr = threonine | 8 |
| Ser = serine | 6 |
| Glx = glutamine (Glu) and/or glutamic acid | 26 |
| Gly = glycine | 22 |
| Ala = alanine | 17 |
| Val = valine | 10 |
| Cys = cysteine | 0 |
| Met = methionine | 4 |
| Ile = isoleucine | 11 |
| Leu = leucine | 12 |
| Tyr = tyrosine | 4 |
| Phe = phenylalanine | 6 |
| Lys = lysine | 16 |
| His = histidine | 7 |
| Arg = arginine | 7 |
| Pro = proline | 12 |

In addition to the biological activity described above, the adhesin protein is immunologically active, i.e., it elicits the formation of antibodies. It is present in S. suis strains independently of the capsular serotype.

The invention thus also relates to the derivatives and fragments of the above-described adhesin protein, which have essentially the same biological or immunological activity as the adhesin protein. A derivative signifies a protein in which part of the amino acids have been substituted, deleted or added, but which nevertheless has retained its essential biological or immunological properties. Substituting or added amino acids include both amino acids occurring in proteins and derivatives of such amino acids. The derivatives according to the invention also include possible aggregates. A fragment signifies a portion of the adhesin protein described, which has retained its essential biological or immunological properties. The derivatives and fragments can be prepared in a manner conventional in protein chemistry. Fragments are preferably prepared by a peptide synthesis e.g. by the solid-phase method. The adhesin and its derivatives or fragments can also be produced by the methods of gene technology. The invention further relates to antibodies raised against the adhesin protein. In this connection, such antibodies also include antibody fragments, such as Fab fragments, or antibody portions expressed in phages which bind to the adhesin protein according to the invention, its derivative or fragment.

Due to its immunological properties the adhesin protein according to the invention, and the derivatives and fragments thereof are also usable as a vaccine against diseases caused by S. suis bacteria, such as septicemia and meningitis in pigs. The vaccine may also contain a polynucleotide coding for the corresponding sequences, optionally in the form of a recombinant organism. The use as a vaccine for humans may also be possible e.g. in the case of groups at risk, such as pig breeders or slaughter workers. Still another possible use of the antibodies would be in passive immunization.

The invention also relates to diagnostic methods for detecting S. suis bacteria or for detecting antibodies directed to S. suis bacteria by utilizing immunoassay methods known per se, such as immuno-fluorescence, ELISA and RIA techniques. To detect the presence of S. suis bacteria in a sample, the sample is contacted with the antibody according to the invention, and the obtained antigen-antibody complexes are then analyzed. Correspondingly, it is possible to detect antibodies directed to S. suis bacteria by reacting the suspected sample with the adhesin protein according to the invention, or a derivative or fragment thereof and analyzing the obtained antigen-antibody complexes. The antigen-antibody complexes may be analyzed either directly or indirectly in a wide variety of ways well-known to one skilled in the art. It is a common practice to immobilize either the antigen or the antibody.

The following non-restrictive examples illustrate the invention.

EXAMPLE 1

Growing *Streptococcus suis* bacteria

The following S. suis strains were used in the studies:
Hemagglutinating: 628, TEW/2, R75/L1, 825 and 752 Non-hemagglutinating: 3027, 1045 and 598/T5
The strains 628, TEW/2, R75/L1 and 825 are described in Kurl, D. N., Haataja, S. and Finne, J., (1989) *Infect. Immun.* 57, 384–389. The other strains were obtained from Dr. J. Hommez, Regional Veterinary Investigation Laboratory, Torhout, Belgium.

The strains were stored frozen in Todd-Hewitt medium at −20° C. The bacteria were grown anaerobically (Gas Pak system) on fresh sheep blood agar plates at 37° C. overnight. The bacteria were harvested from the plates and suspended in phosphate buffer A (10 mM sodium phosphate buffer, 0.15M NaCl, pH 7.4) adjusted to a concentration that gave an $A_{600nm}$ 0.5 at 1:100 dilution.

EXAMPLE 2

Purification of Adhesin Protein

Adhesin protein was detached from the bacterial surface by sonicating 5×15 sec. (chilling on ice for 1–2 min) in 2.5 ml batches into phosphate buffer A. After sonication, protease inhibitor PMSF (phenyl-methylsulphonyl fluoride) was added to a 2 mM concentration. The sonicates were centrifuged at 15,800×g, +8° C., and the supernatants were recovered. The adhesin protein was pre-purified from the mixture by a fractionating ammonium sulphate precipitation. 16 ml of the supernatant was used in the ammonium sulphate precipitation. Other proteins were removed from the mixture by ammonium sulphate having a saturation degree of 60%, and adhesin was precipitated by ammonium sulphate having a saturation degree of 70%. No significant amounts of adhesin protein remained in the 70% supernatant. Cold saturated ammonium sulphate was pipetted into the solution (0° C.), the solution was allowed to stand for 1 h in ice bath, and then centrifuged at 15,800×g, 20 min. Deposits from the 70% precipitation were recovered and dissolved in 16 ml of phosphate buffer B (3.3 mM sodium phosphate buffer, 0.05M NaCl, pH 7.4). The deposits were dialysed overnight at +8° C. against $H_2O$, lyophilized, and dissolved in 4 ml of phosphate buffer A. The purification was monitored in a 6% native polyacrylamide gel electrophoresis by pigeon ovomucoid labelled with radioactive iodine in a Bio Rad minigel device (see Example 3).

The actual purification was performed in a Bio Rad 491 Prep Cell preparative electrophoresis device. 6% native polyacrylamide gel was poured into the cylindrical gel device (the height of the separating gel was 6 cm and that of the stacking gel 2 cm). The total volume of the sample was 4 ml, containing 3,000 μl of the protein solution prepared above, 920 μl of sample buffer (no SDS solution), and 80 μl of staining dye BPB (bromophenol blue). The running solution was 25 mM Tris-192 mM glycine, pH 8.3, and the elution buffer was Tris-HCl, pH 8.3. 4 ml fractions were extracted from the samples, and the fractions were analyzed by measuring their absorbancy at two different wave lengths (214 nm and 280 nm), whereafter the samples were subjected to polyacrylamide gel electrophoresis in the Bio Rad minigel device, as described in Example 3. Fractions 79–83 contained adhesin protein. Fractions 79–81 were combined, dialyzed overnight at +8° C. against phosphate buffer B, and freeze-dried. The dried precipitate was kept at −20° C. for subsequent analyzing.

EXAMPLE 3

Monitoring the Purification

The monitoring of the purification process was based on the observation that *S. suis* bacteria bind intensively pigeon ovomucoid, which contains the galactocyl-α1-4-galactoside of the disaccharide structure. For this reason, an adhesin protein identification method was developed by labelling pigeon ovomucoid radioactively with $^{125}I$ label. In the binding test of the radioactively labelled ovomucoid, the negative, i.e. non-hemagglutinating *S. suis* strain 598/T5 and the weakly hemagglutinating *S. suis* strain 825 were used as control strains in addition to the hemagglutinating *S. suis* strain 628 (the hemagglutination titer of the *S. suis* strain 628 was 64, the titer of the strain 825 was 4, and the titer of the strain 598/T5 was 0). The ovomucoid was labelled radioactively with the $^{125}I$ isotope by the Iodo-Bead method (Pierce Chemical Co, Rockford Ill.) in accordance with the instructions of the manufacturer.

At the first stage, a spot test was developed. In this binding test each bacterial suspension prepared as described in Example 1 was diluted (1:1; 1:10; 1:50) in phosphate buffer A. 1 μl of the suspensions was pipetted onto a gridded nitrocellulose paper, whereafter all extra binding sites were covered by incubation for 1.5 h in phosphate buffer C (0.1M sodium phosphate buffer, 0.5% Tween 20, 150 mM NaCl, pH 5.3). The nitrocellulose was then covered with the $^{125}I$ ovomucoid (about $6 \times 10^5$ cpm, specific activity about $2.5 \times 10^5$ cpm/μg ovomucoid), and incubated for 1 h at +8° C. The membrane was washed 3×10 min in phosphate buffer C, dried between filter papers and exposed to an X-ray film at −80° C. for 24 h. Binding could be detected only in the hemagglutinating strains even at low bacterial concentrations, in addition to which the binding intensity correlated with the hemagglutinating activity.

At the second stage, by applying the above-described method, a Western blot identification method was developed for the adhesin protein in a polyacrylamide gel electrophoresis (Laemmli, U. K. (1970) Nature (London) 227, 680–685). A native gel electrophoresis was used without SDS addition so that the proteins retained their native form. Bacterial sonicates prepared as described in Example 2 were separated in a number of polyacrylamide gel electrophoresis systems containing different concentrations of polyacrylamide (5–9%). Finally the concentration of 6% was used. After the separation the sonicates were transferred by an electric current (60 mA, 30 min) to a PVDFp (Millipore) membrane (Burnette, W. N. (1981) *Anal. Biochem.* 112, 195–203), and the membrane was labelled with the $^{125}I$ ovomucoid as described above. The hemagglutinating *S. suis* strains used in the tests were: 628, TEW/2, R75/L1, 825, 752. The non-hemagglutinating strains were: 3027 and 1045. The sonicates of the hemagglutinating bacterial strains visualized one strong protein band which moved in the electrophoresis at the same rate. The intensity of the band correlated with the hemagglutination activity. However, the negative strains also visualized a band moving at the same rate in the native gel electrophoresis, usually more weakly. The band was thus present in all *S. suis* strains and was not related to the capsular serotypes.

EXAMPLE 4

The Molecular Weight of the Adhesin Protein and the Checking of Purity

The purity of adhesin was checked, and the molecular weight was determined on the basis of the electrophoretic mobility in a 15% SDS polyacrylamide gel electrophoresis (Laemmli, U. K. (1970) *Nature (London)* 227, 680–685). The adhesin protein of the strain 628 (4 μg) was boiled for 5 min in a 2% SDS solution containing either 5% mercaptoethanol or 2.5 mM dithiotreitol. A single band was distinguishable in the purified adhesin protein. Standard proteins Low Molecular Weight Standards manufactured by Pharmacia were used as molecular weight standards. The molecular weight of adhesin was determined to be 18,000.

EXAMPLE 5

Isoelectric Point

Isoelectric focusing was performed in a Phast gel electrophoresis device with the Phast isoelectric system (Pharmacia). The gel was Phast Gel 15531 3-9, and the standards were IEF standard 3–10 (Pharmacia). 0.2 μg of purified adhesin of the strain 628 were used in the determination. The isoelectric focusing gel was stained by using Silver IEF-Method 6 of the Phast system. The isoelectric point of adhesin was determined to be 6.4.

EXAMPLE 6

Amino Acid Analysis

For the amino acid analysis, 7 nmol of purified adhesin of the strain 628 was dissolved in 100 μl of 6M HCl solution.

60 nmol norleucine was added as an internal standard. The solution was hydrolyzed at 110° C. for 24 h, freeze-dried, and analyzed with the LKB 4151 Alpha Plus Aminoacid Analyzer according to the instructions of the manufacturer.

The amino acid composition was as follows:

| | Amino acid | mol amino acid/mol protein |
|---|---|---|
| 1 | Asx | 13.2 |
| 2 | Thr | 8.1 |
| 3 | Ser | 5.8 |
| 4 | Glx | 26.4 |
| 5 | Gly | 22.3 |
| 6 | Ala | 16.9 |
| 7 | Val | 10.3 |
| 8 | Cys | 0.0 |
| 9 | Met | 3.9 |
| 10 | Ile | 11.4 |
| 11 | Leu | 12.3 |
| 12 | Tyr | 3.9 |
| 13 | Phe | 6.0 |
| 14 | Lys | 15.9 |
| 15 | His | 6.6 |
| 16 | Arg | 6.8 |
| 17 | Pro | 12.4 |

EXAMPLE 7

The N-terminal Amino Acid Sequence of the Adhesin Protein

The N-terminal amino acid sequence of the adhesin protein was determined in the Applied Bio-systems 477A Pulsed Liquid Protein/Peptide Sequencer with 120A Amino Acid Analyzer in accordance with the manufacturer's instructions. Purified adhesin was run into a 6% native polyacrylamide gel, from which the adhesin was transferred by an electric current into a PVDFp membrane as described in Example 3. The membrane was stained by the protein dye Coomassie Brilliant Blue (10 min), excessive dye was removed and the protein band was cut off for peptide sequencing.

The N-terminal sequence of the adhesin protein was also determined successfully from the supernatants of the sonicated bacteria: The mobility of the adhesin protein in the native gel electrophoresis is known as the adhesin protein band can be identified on the PVDFp membrane by utilizing the $^{125}$I pigeon ovomucoid. The mobility of the adhesin protein was identified from the five different hemagglutinating S. suis strains (628, TEW/2, R75/L1, 825, 752) in a 6% native polyacrylamide gel electrophoresis; the sonicates of these bacterial strains were subjected to electrophoresis, and the bands were transferred onto a PVDFp membrane. The adhesin bands were cut off from the membrane for amino acid sequencing as described above. The obtained N-terminal sequence was identical for all strains, that is: Ala-Ser-Pro-Ala-Glu-Ile-Ala-Ser-Phe-Ser-Pro-Ala-Pro-Leu-Ala (SEQ ID NO: 1).

EXAMPLE 8

Production of Antibodies Against the Adhesin Protein

Antibodies against the adhesin protein of the strain 628 were produced in Balb/c mice. The mice were immunized either with pure adhesin (10 µg/mouse) or with the sonicate of S. suis (80 µg/mouse). In the former case the adhesin was injected twice in Freund's complete adjuvant (F.C.A.) and once in Freund's incomplete adjuvant (F.I.C.A.). In the latter case the protein mixture was injected into the mice once with F.C.A. and twice mixed with F.I.C.A. The immunization was performed subcutaneously. In both cases, antibodies against the adhesin protein were elicited.

The antibody formation was studied on a PVDFp membrane, onto which the sonicate supernatants of S. suis had been transferred (see Example 2). The band of the adhesin protein was identified (cf. Example 3). (Non-specific binding of the antibodies was prevented by incubating the membrane for 1.5 h in a 1.5% milk powder-0.5% Tween 20 solution in buffer D (10 mM Tris, 150 mM NaCl, pH 7.8). The membrane was washed trice in buffer D, to which 0.05% Tween 20 had been added. The antibody dilutions were added for one hour, whereafter the membrane was washed five times in buffer D, to which 0.05% Tween 20 had been added. The membrane was incubated with anti-mouse antibody labelled with alkaline phosphatase for one hour (1:1,000 dilution), washed five times in buffer D, and the substrate of alkaline phosphatase was added to effect a colour reaction (bromochloroindolyl phosphate/nitro blue tetrazolium). The formation of antibodies against the S. suis strain 628 was strong. The antibodies were still able to specifically recognize the adhesin protein even at a dilution of $1:5\times10^5$.

We claim:

1. An isolated and purified *Streptococcus suis* adhesin protein having a molecular weight of about 18,000 which adhesin protein binds to the Galα1-4Gal disaccharide structure and comprises the amino acid sequence Ala-Ser-Pro-Ala-Glu-Ile-Ala-Ser-Phe-Ser-Pro-Ala-Pro-Leu-Ala (SEQ ID NO: 1).

2. The adhesin protein according to claim 1, wherein said amino acid sequence is the N-terminal sequence.

3. The adhesin protein according to claim 1, wherein said adhesin protein has an isoelectric point of about 6.4.

4. The adhesin protein according to claim 3, wherein said adhesin protein has the following amino acid composition:

| Amino acid | mol amino acid/mol protein |
|---|---|
| Asx | 13 |
| Thr | 8 |
| Ser | 6 |
| Glx | 26 |
| Gly | 22 |
| Ala | 17 |
| Val | 10 |
| Cys | 0 |
| Met | 4 |
| Ile | 11 |
| Leu | 12 |
| Tyr | 4 |
| Phe | 6 |
| Lys | 16 |
| His | 7 |
| Arg | 7 |
| Pro | 12. |

5. A method for producing the *Streptococcus suis* adhesin protein according to claim 1, comprising the steps of:

(a) sonicating a *Streptococcus suis* bacterial strain to detach the adhesin protein;

(b) prepurifying the detached adhesin protein, and thereafter (c) electrophoretically or chromatographically purifying the protein.

6. The method according to claim 5, wherein the protein is purified in step (c) by native gel electrophoresis.

7. A method of identifying a *Streptococcus suis* adhesin protein comprising contacting a sample believed to contain said protein with pigeon ovomucoid or a synthetic derivative containing the Galα1-4Gal disaccharide structure the amount of bound ovomucoid or derivative indicating the amount of adhesin in the sample.

8. Isolated antibody directed to the adhesin protein according to claim 1.

9. Immunoassay method of detecting *Streptococcus suis* bacteria comprising the steps of a) contacting a sample with the antibody of claim 8, and b) analyzing the antigen-antibody complexes obtained, the formation of antigen-antibody complexes indicating the presence or amount of *Streptococcus suis* in the sample.

10. Immunoassay method of detecting antibodies to *Streptococcus suis* bacteria comprising the steps of:

a) contacting a sample with the adhesin protein of claim 1, and b) analyzing the antigen antibody complexes obtained, the formation of antigen-antibody complexes indicating the presence or amount of antibodies to *Streptococcus suis* in the sample.

11. An immunogenic composition comprising the adhesin protein according to claim 1.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: protein ( i i i ) ORIGINAL SOURCE:
        ( A ) ORGANISM: Streptococcus suis
        ( B ) STRAIN: 628, TEW/2, R75/L1, 825 and 752

( i v ) SEQUENCE DESCRIPTION: SEQ ID NO:1:

-continued

| | | | | | | | | | | | | | | |
|---|---|---|---|---|---|---|---|---|---|---|---|---|---|---|
| Ala | Ser | Pro | Ala | Glu | Ile | Ala | Ser | Phe | Ser | Pro | Ala | Pro | Leu | Ala |
| 1 | | | | 5 | | | | | 10 | | | | | 15 |